(12) United States Patent
Nakamura et al.

(10) Patent No.: US 10,894,764 B2
(45) Date of Patent: Jan. 19, 2021

(54) METHOD FOR GRANULATING UREA

(71) Applicant: TOYO ENGINEERING CORPORATION, Tokyo (JP)

(72) Inventors: Shuhei Nakamura, Narashino (JP); Akiko Sugiura, Narashino (JP); Keigo Sasaki, Narashino (JP)

(73) Assignee: TOYO ENGINEERING CORPORATION, Tokyo (JP)

( * ) Notice: Subject to any disclaimer, the term of this patent is extended or adjusted under 35 U.S.C. 154(b) by 0 days.

(21) Appl. No.: 16/494,710

(22) PCT Filed: Mar. 6, 2018

(86) PCT No.: PCT/JP2018/008574
§ 371 (c)(1),
(2) Date: Sep. 16, 2019

(87) PCT Pub. No.: WO2018/168573
PCT Pub. Date: Sep. 20, 2018

(65) Prior Publication Data
US 2020/0002274 A1    Jan. 2, 2020

(30) Foreign Application Priority Data
Mar. 17, 2017    (JP) .................................. 2017-052199

(51) Int. Cl.
*C07C 273/16*    (2006.01)
*B01J 2/00*    (2006.01)
*C07C 275/00*    (2006.01)

(52) U.S. Cl.
CPC ............... *C07C 273/16* (2013.01); *B01J 2/00* (2013.01); *C07C 275/00* (2013.01)

(58) Field of Classification Search
None
See application file for complete search history.

(56) References Cited

U.S. PATENT DOCUMENTS

| | | | |
|---|---|---|---|
| 2011/0229394 A1 | 9/2011 | Niehues et al. | |
| 2012/0240649 A1* | 9/2012 | Meessen | C01C 1/12 71/30 |
| 2015/0133690 A1 | 5/2015 | Mennen et al. | |
| 2018/0037542 A1 | 2/2018 | Nakamura et al. | |

FOREIGN PATENT DOCUMENTS

| | | |
|---|---|---|
| JP | 9-227493 A | 9/1997 |
| JP | 2000-001466 A | 1/2000 |
| JP | 2015-520741 A | 7/2015 |
| WO | WO 2016/159336 A1 | 10/2016 |

OTHER PUBLICATIONS

International Search Report issued in International Patent Application No. PCT/JP2018/008574, dated Mar. 22, 2018.
Search Report issued in European Patent Application No. 18767920.4, dated Nov. 19, 2020.
Potthoff, "Innovative Ammonia Emission Reductions," Nitrogen+ Syngas 294, pp. 39-41 (Jul.-Aug. 2008).

\* cited by examiner

*Primary Examiner* — Amy C Bonaparte
(74) *Attorney, Agent, or Firm* — Foley & Lardner LLP

(57) ABSTRACT

Precipitation of an ammonium salt is prevented while suppressing an increase in water content of the aqueous urea solution which is to be supplied to a urea granulation step, when recovering and using urea and $NH_3$ in a gas which contains urea dust and $NH_3$ and which arises from a urea granulation step.

8 Claims, 3 Drawing Sheets

Prior Art

METHOD FOR GRANULATING UREA

CROSS-REFERENCE TO RELATED APPLICATIONS

This application is the U.S. National Stage of International Patent Application No. PCT/JP2018/008574, filed Mar. 6, 2018, which claims priority from Japanese Patent Application No. 2017-052199, filed Mar. 17, 2017. The contents of these applications are incorporated herein by reference in their entirety.

TECHNICAL FIELD

The present invention relates to a method for granulating urea in which granular solid urea is produced from an aqueous urea solution.

BACKGROUND ART

In a urea plant, urea is synthesized, and then, granular solid urea is produced as a main product. The process flow of a conventional urea granulation process will be described with reference to FIG. 2.

A feed aqueous urea solution containing a trace amount of ammonia is supplied through line 1 to the urea granulation process. A concentrated aqueous recovered-urea solution (line 9), which will be discussed later, is mixed with the feed aqueous urea solution. The liquid mixture (line 11) is transferred to granulation step A. In the granulation step, granular solid urea (line 2) is produced from the aqueous urea solution by using air which is supplied through line 3. From the granulation step, air containing urea dust and ammonia (hereinafter, this air may be referred to as "granulation outlet gas") is withdrawn (line 4) and transferred to recovery step B.

Makeup water (line 5) containing an acid is supplied to recovery step B. In the recovery step, urea dust which has been contained in the granulation outlet gas is recovered in an aqueous recovered-urea solution (line 7); at the same time, ammonia which has been contained in the granulation outlet gas is recovered as an ammonium salt (a salt of the abovementioned acid). On the other hand, an exhaust gas from which urea dust and ammonia have been removed is released to the atmosphere (line 6).

Since the aqueous recovered-urea solution (line 7) contains a large amount of water, this solution cannot be directly treated in granulation step A. Because of this, concentration step C for removing water from the aqueous recovered-urea solution (line 7) to produce a concentrated aqueous recovered-urea solution (line 9), is performed.

The concentrated aqueous recovered-urea solution (line 9), which contains the ammonium salt and which is obtained from concentration step C, is mixed (line 11) with the feed aqueous urea solution which is supplied through line 1 and then supplied to granulation step A. Water which has been removed from the aqueous recovered-urea solution in concentration step C is discharged through line 8.

In such a urea granulation process, since the concentration of the ammonium salt becomes high in concentration step C, the ammonium salt may precipitate. If the ammonium salt precipitates, for example, a strainer of a pump for transporting a concentrated aqueous urea solution and a spray nozzle which is used in the granulation step may be clogged with the precipitates, with the result that a long-term continuous operation may be impossible.

Patent Literature 1 discloses a method for recovering and using urea dust and ammonia which are contained in an exhaust gas. In this method, a first scrubbing tower (for recovering urea dust by an acid-free urea solution) and a second scrubbing tower (for recovering ammonia, and also urea dust which has not been absorbed by the first scrubbing tower, by an aqueous solution containing an acid) are used in a urea recovery step. Further, the total concentration of the ammonium salt and urea in the aqueous recovered-urea solution which is obtained from the second scrubbing tower is set to 20% or more. The aqueous recovered-urea solution is mixed with an aqueous urea solution to be supplied to the granulation step, without being subjected to a concentration step.

In a method which is proposed in Patent Literature 2, a part of urea melt which has been fed to the system is added to an aqueous recovered-urea solution before a concentration step; the concentration of an ammonium salt contained in the urea solution at the outlet of the concentration step (evaporator) is adjusted to less than 12 wt %, in particular, 9 to 11 wt %, and then, the urea solution is supplied to a granulation step; whereas, the rest of the urea melt which has been fed to the system is supplied to the granulation step. In this method, it is recommended that the amount of urea melt to be added to the aqueous recovered-urea solution before the concentration step should be minimum.

PRIOR ART LITERATURES

Patent Literature

Patent Literature 1: JP 2000-1466A
Patent Literature 2: US 2011/0229394 A1

SUMMARY OF THE INVENTION

Problems to be Solved by the Invention

In the method of Patent Literature 1, precipitation of an ammonium salt can be suppressed; however, the recovered solution which is obtained from the second scrubbing tower cannot be concentrated. Because of this, the amount of water in the aqueous urea solution to be supplied to the granulation step may be large, with the result that the water concentration in the resultant product solid urea may become high.

In the method of Patent Literature 2, the ammonium salt may precipitate, because the concentration of the ammonium salt which is contained in the aqueous urea solution after the concentration step is high. Particularly in the case where sulfuric acid is used as the acid, ammonium sulfate precipitates. Thus, it is difficult to use this method in practice.

An object of the present invention is to prevent precipitation of an ammonium salt while suppressing an increase in water content of an aqueous urea solution which is to be supplied to a urea granulation step, when recovering and using urea and ammonia from a gas which contains urea dust and ammonia and which arises from the urea granulation step.

Means for Solving the Problems

The present invention provides a method for granulating urea, including
a granulation step of producing granular solid urea from a feed aqueous urea solution by using air, a recovery step of recovering urea dust and ammonia from air containing urea dust and ammonia discharged from the granulation step, by use of an aqueous solution containing an acid, so as to obtain an aqueous recovered-urea solution which is an aqueous solution containing urea and an ammonium salt;

an ammonium salt concentration adjustment step of mixing the aqueous recovered-urea solution which is obtained from the recovery step with an aqueous urea solution having a relatively low ammonium salt concentration, compared to this aqueous recovered-urea solution, so as to adjust the ammonium salt concentration of the aqueous recovered-urea solution;

a concentration step of concentrating the aqueous recovered-urea solution which is obtained from the ammonium salt concentration adjustment step by vaporizing water which is contained in the aqueous recovered-urea solution which is obtained from the ammonium salt concentration adjustment step, so as to obtain a concentrated aqueous recovered-urea solution; and a mix step of mixing the concentrated aqueous recovered-urea solution with the feed aqueous urea solution, wherein the ammonium salt concentration of the concentrated aqueous recovered-urea solution is 7 mass % or less.

In the ammonium salt concentration adjustment step, a part of the feed aqueous urea solution, before or after the concentrated aqueous recovered-urea solution is mixed, can be used as the abovementioned aqueous urea solution having a relatively low ammonium salt concentration.

The abovementioned granulation method may further include, before the concentration step, a neutralization step of adding an alkali to the aqueous recovered-urea solution which is obtained from the recovery step, so as to neutralize the aqueous recovered-urea solution.

The abovementioned granulation method may further include a control step of controlling the ammonium salt concentration of the concentrated aqueous recovered-urea solution by manipulating the flow rate of the abovementioned "aqueous urea solution having a relatively low ammonium salt concentration" which is to be mixed with the aqueous recovered-urea solution in the ammonium salt concentration adjustment step, based on the present value of the ammonium salt concentration of the concentrated aqueous recovered-urea solution.

In the control step, the present value of the ammonium salt concentration of the concentrated aqueous recovered-urea solution may be obtained based on the temperature and pressure of the water vaporization in the concentration step and the temperature and density of the concentrated aqueous recovered-urea solution.

The acid may be at least one acid selected from the group consisting of sulfuric acid, nitric acid and phosphoric acid.

The abovementioned granulation method may further include a step of supplying the water, which is vaporized in the concentration step, to the recovery step.

Advantages of the Invention

According to the present invention, it is possible to prevent precipitation of an ammonium salt while suppressing an increase in water content of an aqueous urea solution which is to be supplied to a urea granulation step, when recovering and using urea and ammonia from a gas which contains urea dust and ammonia and which arises from the urea granulation step.

EMBODIMENTS FOR CARRYING OUT THE INVENTION

In the present invention, a granulation step, a recovery step, an ammonium salt concentration adjustment step, a concentration step, and a mix step are performed. Hereinafter, embodiments of the present invention will be described with reference to the accompanying drawings; however, the present invention is not limited thereby.

Usually, a feed aqueous urea solution (line 1) to be supplied to the urea granulation process according to the present invention is prepared by separating water from an aqueous urea solution which is obtained from a urea synthesis process to concentrate the aqueous urea solution and to achieve a higher urea concentration. Usually, the urea concentration of the feed aqueous urea solution is 95 mass % or more and 98 mass % or less. The feed aqueous urea solution contains a trace amount of free ammonia derived from the urea synthesis process. The ammonia concentration of the feed aqueous urea solution is usually 1000 to 1500 mass ppm. Usually, in the granulation step, a trace amount of ammonia is generated as a result of hydrolysis and the biuret formation reaction in the aqueous urea solution.

[Granulation Step A]

Figure 1:
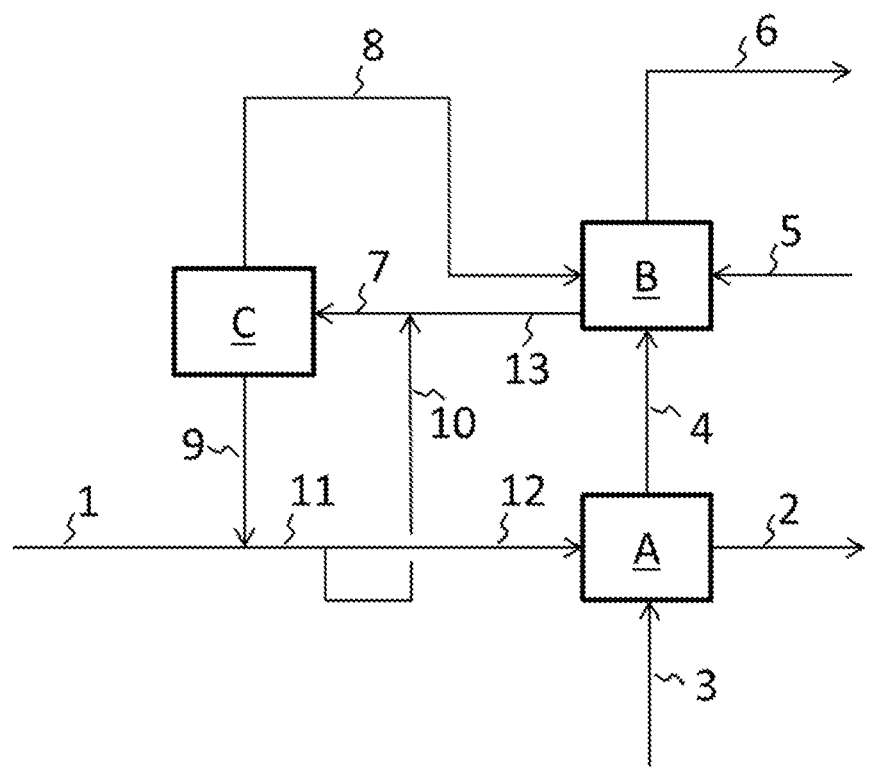
FIG. 1 is a process flow diagram for illustrating an embodiment of the urea granulation method according to the present invention.
Figure 2:
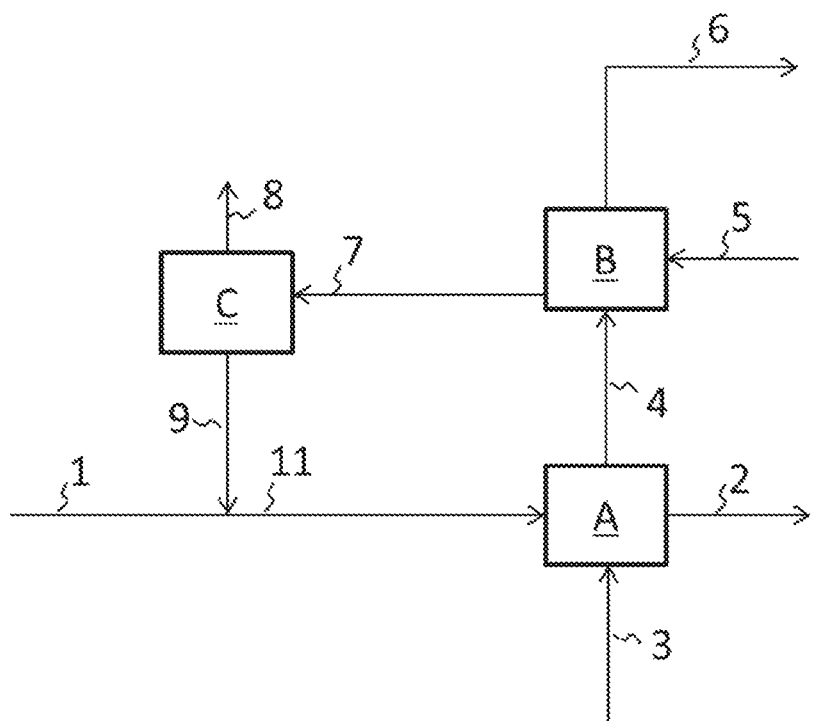
FIG. 2 is a process flow diagram for illustrating a conventional urea granulation method.

As shown in FIG. 1, the feed aqueous urea solution which is supplied through line 1 is transferred to granulation step A. In granulation step A, granular solid urea is produced from the feed aqueous urea solution by using air. It should be noted that, since the concentrated aqueous recovered-urea solution (line 9) is mixed with the feed aqueous urea solution (line 1), granular solid urea is produced from the feed aqueous urea solution, and at the same time, granular solid urea is also produced from the concentrated aqueous recovered-urea solution, in granulation step A. In the process shown in FIG. 1, the line for the liquid mixture (line 11) of the feed aqueous urea solution and the concentrated aqueous recovered-urea solution is branched and a part (line 12) of the solution is supplied to granulation step A; whereas, the rest part (line 10) is mixed with the aqueous recovered-urea solution (line 13) in the ammonium salt concentration adjustment step. Accordingly, the urea in the aqueous urea solution which is introduced to granulation step A through line 12 is cooled and solidified by air supplied through line 3 to form solid urea, which is withdrawn as a product through line 2.

In granulation step A, solid urea can be produced by using a known granulator as appropriate. For example, a urea granulator which employs a fluid bed or a spout-fluid bed, is used as the granulator. As the granulator, a prilling urea production apparatus (for example, Prilling Tower) may be used. The shape and size of solid urea particles are not particularly limited and can be determined as appropriate.

The air (granulation outlet gas) (line 4) containing urea dust and ammonia is withdrawn from granulation step A. Typically, the concentration of urea dust is 3000 to 10000 mass ppm and the concentration of ammonia is 100 to 300 mass ppm in the gas in line 4.

Besides the granulator, a cooler for cooling solid urea which is discharged from granulation step A may be provided to line 2. Air may be used for the cooling in this cooler. The air which is discharged from the cooler may contain urea dust and also ammonia. Accordingly, the air which is discharged from the cooler may be treated in the recovery step in the same manner as the air which is discharged from the granulation step.

The composition of the solid urea varies depending on the individual specifications required. Typically, the solid urea contains, for example, 98.5 to 99.5 mass % of urea, 0.1 to 0.5 mass % of water content, and 0.2 to 1.0 mass % of the ammonium salt.

[Recovery Step B]

In recovery step B, urea dust and ammonia are recovered from the granulation outlet gas (line 4) by use of an aqueous solution containing an acid to obtain the aqueous recovered-urea solution (line 13).

There may be used, as a recovery apparatus, a known scrubbing tower, such as a packed bed scrubber (filled with packing) or a venturi scrubber. Usually, a scrubbing liquid is circulated within the scrubbing tower so that the scrubbing liquid is brought into gas-liquid contact with the granulation outlet gas. In this manner, urea dust and ammonia are recovered with the scrubbing liquid. In order to discharge urea and an ammonium salt from the recovery apparatus, a part of the scrubbing liquid (aqueous solution mixture containing urea, the ammonium salt and the acid) is withdrawn from the recovery apparatus as the aqueous recovered-urea solution (line 13). The rest of the scrubbing liquid is circulated to the recovery apparatus and is brought into contact with the granulation outlet gas. Water (makeup water) containing an acid is supplied to the recovery apparatus. In short, in recovery step B, urea dust and ammonia in the granulation outlet gas are absorbed in the aqueous solution containing the acid. At this time, ammonia is absorbed as the ammonium salt.

Typically, the pH of the scrubbing liquid (liquid to be brought into contact with a gas containing urea dust and ammonia) may be adjusted to about 2 to 7 by use of an acid. As the acid, at least one selected from the group consisting of sulfuric acid, nitric acid and phosphoric acid may be used. In particular, sulfuric acid may be used.

Air in which urea and ammonia concentrations have been reduced is discharged as an exhaust gas from recovery step B (line 6).

In the process shown in FIG. 1, the makeup water (line 5) containing the acid, and also water (line 8; this water may contain urea, the ammonium salt and ammonia in low concentrations) which is obtained from concentration step C are used as makeup water to be supplied to the recovery step.

The scrubbing liquid to be brought into contact with the granulation outlet gas may contain urea in a concentration of, for example, 40 to 60 mass %, an ammonium salt in a concentration of, for example 1 to 10 mass % and have pH of, for example, 2 to 7. The same is true for the aqueous recovered-urea solution (line 13).

The makeup water through line 5 and the makeup water through line 8 are used for the purpose of diluting the scrubbing liquid to be brought into contact with the granulation outlet gas. Accordingly, the urea concentration and ammonia concentration of the makeup water can lower than that of the scrubbing liquid. For example, both the urea concentration and ammonia concentration of the makeup water may be 1 mass % or less. More specifically, the water in line 8 contains, for example, 0 to 0.5 mass % of urea, 0 to 0.5 mass % of ammonia, and 0 to 0.01 mass % of the ammonium salt. The makeup water of line 5 contains, for example, 0 to 5 mass ppm of urea and 0 to 5 mass ppm of ammonia.

As to the urea and ammonia concentrations in the exhaust gas, usually, the concentration of urea is, for example, 30 to 50 mass ppm and the concentration of ammonia is 30 to 50 mass ppm.

[Ammonium Salt Concentration Adjustment Step]

The aqueous recovered-urea solution (line 13) which is obtained from the recovery step is mixed with an aqueous urea solution (hereinafter sometimes referred to as "low ammonium salt concentration aqueous urea solution") having a relatively low ammonium salt concentration, compared to the aqueous recovered-urea solution. Thereby, the concentration of the ammonium salt in the aqueous recovered-urea solution is adjusted. In other words, the aqueous urea solution (line 10) having a lower ammonium salt concentration than the aqueous recovered-urea solution (line 13) is added to the aqueous recovered-urea solution (line 13) to obtain an aqueous recovered-urea solution (line 7) which is reduced in ammonium salt concentration. The amount of the "low ammonium salt concentration aqueous urea solution" to be mixed is determined so that the ammonium salt concentration of the concentrated aqueous recovered-urea solution (line 9) becomes 7 mass % or less.

In the process shown in FIG. 1, there is used as the "low ammonium salt concentration aqueous urea solution", a part (line 10) of the liquid mixture (line 11) of the feed aqueous urea solution (line 1) and the concentrated aqueous recovered-urea solution (line 9). In other words, a part (line 10) of the feed aqueous urea solution with which the concentrated aqueous recovered-urea solution has been mixed, is used as the "low ammonium salt concentration aqueous urea solution" in the ammonium salt concentration adjustment step.

Figure 3:
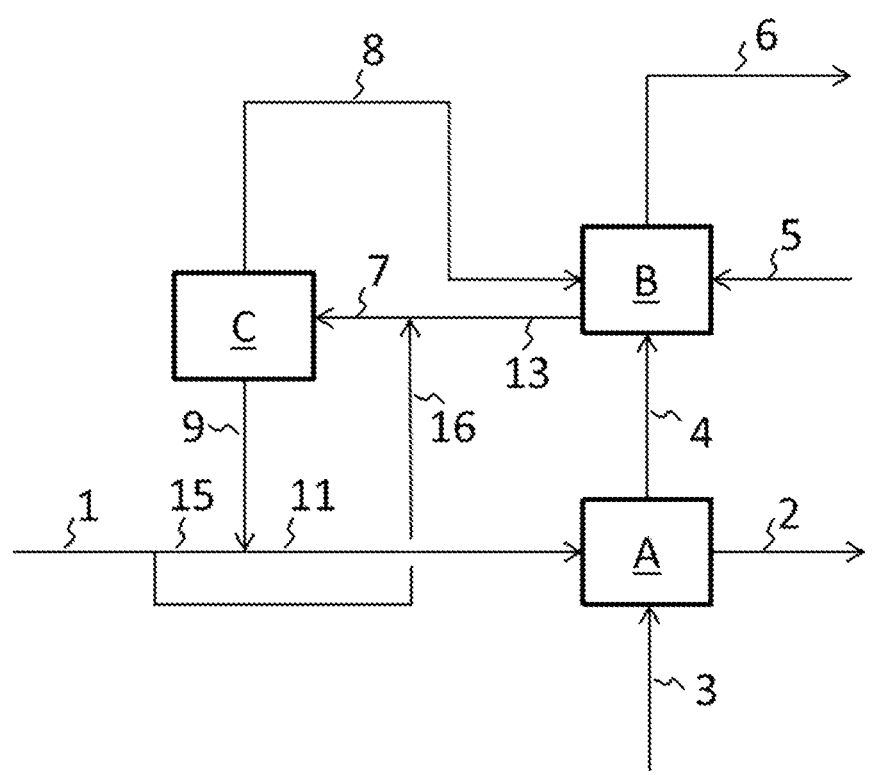
FIG. 3 is a process flow diagram for illustrating another embodiment of the urea granulation method according to the present invention.

Alternatively, as shown in FIG. 3, the feed aqueous urea solution (line 1) is branched and a branched part (line 16) may be used as the "low ammonium salt concentration aqueous urea solution" and mixed with the aqueous recovered-urea solution (line 13). In other words, a part (line 16) of the feed aqueous urea solution before the concentrated aqueous recovered-urea solution is mixed may be used as the "low ammonium salt concentration aqueous urea solution" in the ammonium salt concentration adjustment step. In this case, the rest (line 15) of the feed aqueous urea solution is mixed with the concentrated aqueous recovered-urea solution (line 9) and the resultant liquid mixture (line 11) may be supplied to granulation step A.

[Concentration Step C]

In the concentration step, water which is contained in the aqueous recovered-urea solution (line 7) which is obtained from the ammonium salt concentration adjustment step is vaporized, thereby concentrating the aqueous recovered-urea solution to obtain the concentrated aqueous recovered-urea solution (line 9).

In order to prevent precipitation of an ammonium salt, the concentration of an ammonium salt (in particular, ammonium sulfate) which is contained in the concentrated aqueous recovered-urea solution (line 9) is preferably 7 mass % or less. In order to cause the ammonium salt concentration to be low in the concentrated aqueous recovered-urea solution as mentioned above, the ammonium salt concentration of the solution is adjusted (in particular, reduced) in the ammonium salt concentration adjustment step. The ammonium salt concentration of the concentrated aqueous recovered-urea solution may be, for example, 0.01 mass % or more.

In order to obtain a solution (line 12 in FIG. 1) which can be suitably treated in the granulation step, the water concentration in the concentrated aqueous recovered-urea solution (line 9) is preferably 5 mass % or less. By using an appropriate concentration method such as a vacuum concentration method, the water concentration of the concentrated aqueous recovered-urea solution can be decreased to a concentration of 0.2 mass % or more, for example.

Water which is vaporized from the aqueous recovered-urea solution in concentration step C contains urea, an ammonium salt, and ammonia which is generated in concentration step C; however, since their concentrations are low, this water can be used as the makeup water in recovery step B via line 8. In this manner, water containing an ammonium salt can be kept within the system. Water of line 8 may be condensed, and then supplied to recovery step B in the form of liquid, or may be supplied to recovery step B in the form of steam (in this case, steam is condensed in an apparatus used in the recovery step).

In the concentration step, a known evaporator which can vaporize water may be used as appropriate. For example, water can be vaporized by heating, for example, by use of an evaporator having a heat transfer tube.

[Mix Step]

The concentrated aqueous recovered-urea solution (line 9) which is concentrated in concentration step C is mixed with the feed aqueous urea solution which is supplied through line 1. In the process shown in FIG. 1, the feed aqueous urea solution (line 1) is entirely mixed with the concentrated aqueous recovered-urea solution (line 9), and a part (line 12) of the resultant liquid mixture (line 11) is supplied to granulation step A. In the process shown in FIG. 3, a part (line 15) of the feed aqueous urea solution and the concentrated aqueous recovered-urea solution (line 9) are mixed and the resultant liquid mixture (11) is entirely supplied to granulation step A.

In the mix step, a known technique for mixing liquids with each other can be used as appropriate.

[Neutralization Step]

As necessary, an alkali may be added to the aqueous recovered-urea solution (line 13), which is obtained from recovery step B, to neutralize the aqueous recovered-urea solution.

In recovery step B, if the acid which is used for absorbing ammonia is excessively used compared to the amount of ammonia, the absorption efficiency can be increased. However, in a particular case where sulfuric acid is used, stainless steel may be corroded by residual sulfuric acid and heat which is applied in the concentration step. Therefore, stainless steel may not be used in the concentration apparatus which is used in the concentration step, and extremely expensive zirconium may have to be used. In such a case, the neutralization step may be performed before the concentration step to neutralize the acid, so that stainless steel can be used.

As the neutralization method, a known neutralization method of neutralizing an acid with an alkali may be used as appropriate. In particular, it is possible to neutralize the aqueous recovered-urea solution (line 13), by adding ammonia to the aqueous recovered-urea solution (line 13) before the "low ammonium salt concentration aqueous urea solution" (line 10) and the aqueous recovered-urea solution are mixed.

[Control Step]

It is possible to control the ammonium salt concentration of the concentrated aqueous recovered-urea solution (line 9) to a target value (SV), by manipulating the flow rate of the "low ammonium salt concentration aqueous urea solution" (line 10 in FIG. 1, line 16 in FIG. 3) which is to be mixed with the aqueous recovered-urea solution (line 13) in the ammonium salt concentration adjustment step, based on the present value (PV) of the ammonium salt concentration of the concentrated aqueous recovered-urea solution (line 9).

To this end, the present value (PV) of the ammonium salt concentration of the concentrated aqueous recovered-urea solution can be obtained based on the temperature and pressure of the water vaporization in the concentration step and the temperature and density of the concentrated aqueous recovered-urea solution (line 9).

It is possible to know the temperature and pressure of the water vaporization in the concentration step as appropriate. This temperature and pressure can be measured by, for example, an appropriate thermometer and pressure gauge provided in the evaporator which is used for the concentration. It is also possible to know the temperature and density of the concentrated aqueous recovered-urea solution as appropriate. This temperature and density can be measured by, for example, providing a thermometer and density meter to line 9. If the difference between the water vaporization temperature and the temperature of the concentrated aqueous recovered-urea solution can be ignored, either the water vaporization temperature or the temperature of the concentrated aqueous recovered-urea solution is measured and the measured value can be used as both of the temperature values.

Based on these temperatures, pressure, and density, the present value of the ammonium salt concentration of the concentrated aqueous recovered-urea solution can be obtained. It is easy to measure these temperatures, pressure and density online in real time. Accordingly, the present value (PV) of the ammonium salt concentration of the concentrated aqueous recovered-urea solution can be obtained based on these values, thereby controlling the ammonium salt concentration of the concentrated aqueous recovered-urea solution to a target value (SV) in real time.

In order to manipulate the flow rate of the "low ammonium salt concentration aqueous urea solution" (line 10 in FIG. 1, line 16 in FIG. 3), a known flow control unit such as a flow control valve, may be used as appropriate.

A specific procedure for obtaining the present value (PV) of the ammonium salt concentration of the concentrated aqueous recovered-urea solution is discussed below. It should be noted that the aqueous recovered-urea solution is considered to be a three-component system substantially consisting of urea, an ammonium salt (for example, ammonium sulfate), and water.

Determination of Water Concentration of Concentrated Aqueous Recovered-Urea Solution:

The vapor pressure of water of a three-component aqueous urea solution substantially consisting of urea, an ammonium salt, and water, such as the aqueous recovered-urea solution (line 7) and the concentrated aqueous recovered-urea solution (line 9), is determined by the temperature and water concentration of the three-component aqueous urea solution. If the temperature and pressure stay constant, water of the three-component aqueous urea solution vaporizes until the partial pressure of the water reaches the vapor pressure, which means that the three-component aqueous urea solution is concentrated. At this time, because almost all of the substances which are vaporized from the three-component aqueous urea solution are water (although negligible amounts of ammonia and carbon dioxide are vaporized), the partial pressure of water can be regarded as being equal to the operating pressure. Accordingly, if the temperature and pressure of the water vaporization in the concentration step are determined, the water concentration of the concentrated aqueous recovered-urea solution can be estimated. At this time, a correlation amongst the temperature, vapor pressure of water, and water concentration of the three-component aqueous urea solution can be used. This correlation may be obtained by a preliminary experiment.

Determination of Urea Concentration and Ammonium Salt Concentration of Concentrated Aqueous Recovered-Urea Solution:

Because the water concentration of the concentrated aqueous recovered-urea solution is determined as described above, the concentration of the remaining components (total concentration of urea and the ammonium salt) in the concentrated aqueous recovered-urea solution can be determined. The densities of the ammonium salt and the urea are different from each other. Therefore, if the density of the concentrated aqueous recovered-urea solution is determined, the ratio of the urea and the ammonium salt can be estimated. In order to correct the effect of the temperature on the density, the temperature may be measured together with the density. In order to estimate the ratio of the urea and the ammonium salt, it is possible to use a correlation amongst the water concentration, density, and temperature of a two-component liquid mixture consisting of urea and water, and a correlation between the density and temperature of ammonium sulfate can be used. These correlations can be obtained by preliminary experiments.

The control step may be automatically carried out by using an appropriate instrumentation control system.

According to the present invention, precipitation of an ammonium salt can be prevented. Accordingly, it is possible to prevent clogging of, for example, a strainer of a pump for transporting a concentrated aqueous urea solution and a spray nozzle which is used in a granulation step, which enables a long-term continuous operation. In addition, by concentrating an aqueous urea solution containing an ammonium salt, an increase in the water content of the aqueous urea solution transferred to a granulation step can be suppressed.

EXAMPLES

Hereinafter, the present invention will be more specifically described based on Examples. However, the present invention is not limited thereto.

Example 1

Process simulation was carried out for the process flow shown in FIG. 1. The results are shown in Table 1.

A feed aqueous urea solution (urea: 95.9 mass %, ammonia: 0.1 mass %, water 4.0 mass %) was supplied through line 1 at a temperature of 132° C., a pressure of 10.0 kg/cm$^2$G (0.981 MPaG) and a flow rate of 128.9 t/h. The letter "G" in the pressure unit means that the pressure is gauge pressure.

It was assumed that the feed aqueous urea solution (line 1) contained 1000 mass ppm (0.128 t/h) of free ammonia; that free ammonia was generated at a rate of 0.03 t/h by the biuret formation reaction in granulation step A; and that this ammonia (0.158 t/h) was entirely transferred into air in granulation step A and was contained in the gas of line 4.

The concentrated aqueous recovered-urea solution (line 9) having a temperature of 132° C., a pressure of 10.0 kg/cm$^2$G (0.981 MPaG), and a flow rate of 18.3 t/h was mixed with the feed aqueous urea solution (line 1). The resultant liquid mixture (line 11) was divided (branched) into a stream (line 10) having a flow rate of 12.5 t/h and a stream (line 12) having a flow rate of 134.8 t/h. The former stream was used as the "low ammonium salt concentration aqueous urea solution" and the latter stream was supplied to granulation step A. From granulation step A, air (line 4) containing 0.5 mass % of urea dust and 0.01 mass % of ammonia and further containing 1.5 mass % of water content was discharged and transferred to recovery step B. Further, from granulation step A, solid urea (line 2) containing 0.2 mass % of water and 0.5 mass % of ammonium sulfate was obtained as a product.

Water which is supplied through line 8 is supplied as makeup water to recovery step B, in addition to makeup water (line 5) containing sulfuric acid. The concentrations of urea and ammonia in the exhaust gas discharged from recovery step B to line 6 were both set to be 30 to 50 mass ppm. In the recovery step, urea and ammonia which were contained in the gas of line 4 were recovered into the aqueous recovered-urea solution (line 13). At this time, ammonia in this gas reacted with the sulfuric acid which was supplied through line 5, and was recovered into the aqueous recovered-urea solution as an ammonium sulfate.

The aqueous recovered-urea solution (line 13) and the "low ammonium salt concentration aqueous urea solution" (line 10) were mixed (ammonium salt concentration adjustment step). The resultant liquid mixture (aqueous urea solution whose ammonium salt concentration had been adjusted) was supplied through line 7 to the concentration step. The ammonium sulfate concentration of the "low ammonium salt concentration aqueous urea solution" (line 10) was 0.5 mass % and the ammonium sulfate concentration of the aqueous recovered-urea solution (line 13) was 4.9 mass %. The former concentration was lower than the latter one (about 1/10).

The temperature of the aqueous recovered-urea solution (line 13) was 40° C. The temperature of the liquid mixture (line 7) which was to be supplied to concentration step C was 115° C. Because corrosion occurs at a high temperature, if a step of neutralizing an acid in the aqueous urea solution to be supplied to the concentration step is carried out, the neutralizing is preferably carried out at a lower temperature. Specifically, an alkali (for example, ammonia) is preferably added to the aqueous recovered-urea solution (line 13) having a temperature of 40° C.

In the concentration step, the aqueous urea solution (line 7) whose ammonium salt concentration had been adjusted was heated to vaporize water to obtain the concentrated aqueous recovered-urea solution (line 9) in which urea was concentrated. The flow rate of the "low ammonium salt concentration aqueous urea solution" (line 10) was determined so that the ammonium sulfate concentration in line 9 became 3.7 mass %.

Steam (containing none of urea, an ammonium salt and an acid) which was obtained by vaporizing water was supplied through line 8 to recovery step B.

Heating, cooling, and increasing and reducing pressure of a fluid were performed as necessary by an appropriate means (e.g., heat exchanger, pump, blower, pressure reducing valve), although these are not shown in FIG. 1 and FIG. 3. More specifically, the aqueous recovered-urea solution (line 13) was heated (so that the liquid temperature of line 7 became 115° C.) by a heat exchanger, before the aqueous recovered-urea solution and the "low ammonium salt concentration aqueous urea solution" (line 10) were mixed. In concentration step C, water was vaporized by an evaporator which was placed under a negative pressure by an ejector. The resultant concentrated aqueous recovered-urea solution was pressurized by a pump to 10.0 kg/cm$^2$G (0.981 MPaG) and transferred to line 9. A granulator which was used in granulation step A and also line 4 were kept at a negative pressure(s) and the gas which was withdrawn from recovery step B was pressurized by a blower and discharged to line 6.

Hereinafter, there will be described a procedure for estimating the concentration of an ammonium salt based on the temperature, pressure and density for the concentrated aqueous recovered-urea solution (line 9).

The concentrated aqueous recovered-urea solution consists of three-components: urea, ammonium sulfate and water. A correlation amongst the temperature, vapor pressure of water, and water concentration of a three-component aqueous urea solution consisting of urea, an ammonium salt and water was obtained from a preliminary experiment. By using this correlation, there was obtained the water concentration at which the water vapor pressure of the three-component aqueous urea solution at 132° C. equaled the pressure of concentration step C of −0.7 kg/cm$^2$G (−0.068 MPaG). The obtained water concentration was 4 mass %. In other words, the water concentration of the concentrated aqueous recovered-urea solution was 4 mass %.

The density of a two-component liquid mixture consisting of water (4 mass %) and urea (96 mass %) and the density of ammonium sulfate (pure substance) can be estimated if the temperature is determined. It is possible to estimate, from the densities which have been estimated as mentioned above and the density (measured value) of the concentrated aqueous recovered-urea solution, a mixing ratio between the two-component liquid mixture and ammonium sulfate so that the two-component liquid mixture and ammonium sulfate are mixed to obtain a liquid having the same composition as that of the concentrated aqueous recovered-urea solution. As an example, there will be described a case in which the concentrated aqueous recovered-urea solution has a density (measured value) of 1204.8 kg/m$^3$ and a temperature of 132° C. At a temperature of 132° C., the density of the two-component liquid mixture is 1193.6 kg/m$^3$ and the density of ammonium sulfate is 1499.6 kg/m$^3$. The correlation amongst the water concentration, density and temperature of the two-component liquid mixture and the correlation between the density and temperature of ammonium sulfate have been obtained by preliminary experiments.

If the two-component liquid mixture and ammonium sulfate are mixed to obtain a solution having the same composition as that of the concentrated aqueous recovered-urea solution, the following equation is established.

$$1193.6 \times (1-c) + 1499.6 \times c = 1204.8$$

where c is the ratio of the mass of ammonium sulfate relative to the total mass of the two-component liquid mixture and ammonium sulfate (in other words, the mass of the concentrated aqueous recovered-urea solution).

The value of the abovementioned c is found to be 0.037 (3.7 mass %). In other words, in the concentrated aqueous recovered-urea solution, water concentration is found to be 4 mass % and the concentration of ammonium sulfate is found to be 3.7 mass %. Therefore, the urea concentration is 92.3 mass %.

Comparative Example 1

Process simulation was carried out in the same manner as Example 1 except that the flow rate of the stream through line 10 was set to be zero. In other words, the aqueous recovered-urea solution obtained from the recovery step was directly supplied to the concentration step without adjusting the concentration of an ammonium salt.

In Comparative Example 1, the ammonium sulfate concentration of the concentrated aqueous recovered-urea solution (line 9) was 10.5 mass %. In this case, ammonium sulfate is liable to precipitate in the concentration step, in line 9 and downstream lines thereof or in the granulation step.

In Example 1, the ammonium sulfate concentration of the concentrated aqueous recovered-urea solution (line 9) was 3.7 mass %. In Example 1, ammonium sulfate precipitation can be prevented.

As is apparent from comparison between Example 1 and Comparative Example 1, according the present invention, the "low ammonium salt concentration aqueous urea solution" is mixed with the aqueous recovered-urea solution before the concentration step, thereby decreasing the ammonium salt concentration of the aqueous urea solution; and then, water is removed in the concentration step. Owing to this, precipitation of the ammonium salt can be prevented.

The density of the concentrated aqueous recovered-urea solution (line 9) was 1205 kg/m$^3$ in Example 1 and 1226 kg/m$^3$ in Comparative Example 1.

TABLE 1

Simulation results of Example 1

| | \multicolumn{14}{c}{Line No.} |
| | 1 | | 2 | | 3 | | 4 | | 5 | | 6 | | 13 | |
| | t/h | Mass % | t/h | Mass % | t/h | Mass % | t/h | Mass % | t/h | Mass % | t/h | Mass % | t/h | Mass % |
| --- | --- | --- | --- | --- | --- | --- | --- | --- | --- | --- | --- | --- | --- | --- |
| Urea | 123.6 | 95.9 | 123.6 | 99.3 | 0.0 | 0.0 | 5.0 | 0.5 | 0.0 | 0.0 | 0.0 | 0.0 | 5.0 | 40.1 |
| NH3 | 0.1 | 0.1 | 0.0 | 0.0 | 0.0 | 0.0 | 0.2 | 0.01 | 0.0 | 0.0 | 0.0 | 0.0 | 0.0 | 0.0 |
| Water | 5.2 | 4.0 | 0.3 | 0.2 | 11.7 | 1.1 | 16.8 | 1.5 | 0.0 | 2.0 | 45.0 | 4.1 | 6.9 | 55.0 |
| Ammonium sulfate | 0.0 | 0.0 | 0.6 | 0.5 | 0.0 | 0.0 | 0.0 | 0.0 | 0.0 | 0.0 | 0.0 | 0.0 | 0.6 | 4.9 |
| Sulfuric acid | 0.0 | 0.0 | 0.0 | 0.0 | 0.0 | 0.0 | 0.0 | 0.0 | 0.5 | 98.0 | 0.0 | 0.0 | 0.0 | 0.0 |
| Air | 0.0 | 0.0 | 0.0 | 0.0 | 1060.5 | 98.9 | 1060.5 | 98.0 | 0.0 | 0.0 | 1060.5 | 95.9 | 0.0 | 0.0 |
| Total | 128.9 | 100.0 | 124.5 | 100.0 | 1072.2 | 100.0 | 1082.4 | 100.0 | 0.5 | 100.0 | 1105.5 | 100.0 | 12.5 | 100.0 |
| Pressure | 10.0 kg/cm2G | | 0.0 kg/cm2G | | 0.04 kg/cm2G | | −0.002 kg/cm2G | | 3.0 kg/cm2G | | 0.0 kg/cm2G | | 3.0 kg/cm2G | |
| | 0.981 MPaG | | 0.000 MPaG | | 0.004 MPaG | | −0.0002 MPaG | | 0.294 MPaG | | 0.000 MPaG | | 0.294 MPaG | |

TABLE 1-continued

Simulation results of Example 1

| | | | | | | | | | | | | |
|---|---|---|---|---|---|---|---|---|---|---|---|---|
| Temperature | 132 | °C. | 50 | °C. | 35 | °C. | 100 | °C. | 30 | °C. | 40 | °C. | 40 | °C. |
| Density | — | | — | | — | | — | | — | | — | | — | |

| | Line No. | | | | | | | | | | | |
|---|---|---|---|---|---|---|---|---|---|---|---|---|
| | 7 | | 8 | | 9 | | 10 | | 11 | | 12 | |
| | t/h | Mass % | t/h | Mass % | t/h | Mass % | t/h | Mass % | t/h | Mass % | t/h | Mass % |
| Urea | 16.9 | 67.8 | 0.0 | 0.0 | 16.9 | 92.3 | 11.9 | 95.5 | 140.5 | 95.5 | 128.6 | 95.5 |
| NH3 | 0.0 | 0.0 | 0.0 | 0.2 | 0.0 | 0.0 | 0.0 | 0.1 | 0.1 | 0.1 | 0.1 | 0.1 |
| Water | 7.4 | 29.5 | 6.6 | 99.8 | 0.7 | 4.0 | 0.5 | 4.0 | 5.9 | 4.0 | 5.4 | 4.0 |
| Ammonium sulfate | 0.7 | 2.7 | 0.0 | 0.0 | 0.7 | 3.7 | 0.1 | 0.5 | 0.7 | 0.5 | 0.6 | 0.5 |
| Sulfuric acid | 0.0 | 0.0 | 0.0 | 0.0 | 0.0 | 0.0 | 0.0 | 0.0 | 0.0 | 0.0 | 0.0 | 0.0 |
| Air | 0.0 | 0.0 | 0.0 | 0.0 | 0.0 | 0.0 | 0.0 | 0.0 | 0.0 | 0.0 | 0.0 | 0.0 |
| Total | 24.9 | 100.0 | 6.6 | 100.0 | 18.3 | 100.0 | 12.5 | 100.0 | 147.2 | 100.0 | 134.8 | 100.0 |
| Pressure | 3.0 | kg/cm2G | −0.7 | kg/cm2G | 10.0 | kg/cm2G | 10.0 | kg/cm2G | 10.0 | kg/cm2G | 10.0 | kg/cm2G |
| | 0.294 | MPaG | −0.068 | MPaG | 0.981 | MPaG | 0.981 | MPaG | 0.981 | MPaG | 0.981 | MPaG |
| Temperature | 115 | °C. | 132 | °C. | 132 | °C. | 132 | °C. | 132 | °C. | 132 | °C. |
| Density | — | | — | | 1205 | kg/m3 | — | | — | | — | |

TABLE 2

Simulation results of Comparative Example 1

| | Line No. | | | | | | | | | | | |
|---|---|---|---|---|---|---|---|---|---|---|---|---|
| | 1 | | 2 | | 3 | | 4 | | 5 | | 6 | | 13 | |
| | t/h | Mass % | t/h | Mass % | t/h | Mass % | t/h | Mass % | t/h | Mass % | t/h | Mass % | t/h | Mass % |
| Urea | 123.6 | 95.9 | 123.6 | 99.3 | 0.0 | 0.0 | 5.0 | 0.5 | 0.0 | 0.0 | 0.0 | 0.0 | 5.0 | 40.1 |
| NH3 | 0.1 | 0.1 | 0.0 | 0.0 | 0.0 | 0.0 | 0.2 | 0.01 | 0.0 | 0.0 | 0.0 | 0.0 | 0.0 | 0.0 |
| Water | 5.2 | 4.0 | 0.3 | 0.2 | 11.7 | 1.1 | 16.8 | 1.5 | 0.0 | 2.0 | 45.0 | 4.1 | 6.9 | 55.0 |
| Ammonium sulfate | 0.0 | 0.0 | 0.6 | 0.5 | 0.0 | 0.0 | 0.0 | 0.0 | 0.0 | 0.0 | 0.0 | 0.0 | 0.6 | 4.9 |
| Sulfuric acid | 0.0 | 0.0 | 0.0 | 0.0 | 0.0 | 0.0 | 0.0 | 0.0 | 0.5 | 98.0 | 0.0 | 0.0 | 0.0 | 0.0 |
| Air | 0.0 | 0.0 | 0.0 | 0.0 | 1060.5 | 98.9 | 1060.5 | 98.0 | 0.0 | 0.0 | 1060.5 | 95.9 | 0.0 | 0.0 |
| Total | 128.9 | 100.0 | 124.5 | 100.0 | 1072.2 | 100.0 | 1082.4 | 100.0 | 0.5 | 100.0 | 1105.5 | 100.0 | 12.5 | 100.0 |
| Pressure | 10.0 | kg/cm2G | 0.0 | kg/cm2G | 0.04 | kg/cm2G | −0.002 | kg/cm2G | 3.0 | kg/cm2G | 0.0 | kg/cm2G | 3.0 | kg/cm2G |
| | 0.981 | MPaG | 0.000 | MPaG | 0.004 | MPaG | 0.000 | MPaG | 0.294 | MPaG | 0.000 | MPaG | 0.294 | MPaG |
| Temperature | 132 | °C. | 50 | °C. | 35 | °C. | 100 | °C. | 30 | °C. | 40 | °C. | 40 | °C. |
| Density | — | | — | | — | | — | | — | | — | | — | |

| | Line No. | | | | | | | | | | | |
|---|---|---|---|---|---|---|---|---|---|---|---|---|
| | 7 | | 8 | | 9 | | 10 | | 11 | | 12 | |
| | t/h | Mass % | t/h | Mass % | t/h | Mass % | t/h | Mass % | t/h | Mass % | t/h | Mass % |
| Urea | 5.0 | 40.1 | 0.0 | 0.0 | 5.0 | 85.5 | 0.0 | — | 128.6 | 95.5 | 128.6 | 95.5 |
| NH3 | 0.0 | 0.0 | 0.0 | 0.0 | 0.0 | 0.0 | 0.0 | — | 0.1 | 0.1 | 0.1 | 0.1 |
| Water | 6.9 | 55.0 | 6.6 | 100.0 | 0.2 | 4.0 | 0.0 | — | 5.4 | 4.0 | 5.4 | 4.0 |
| Ammonium sulfate | 0.6 | 4.9 | 0.0 | 0.0 | 0.6 | 10.5 | 0.0 | — | 0.6 | 0.5 | 0.6 | 0.5 |
| Sulfuric acid | 0.0 | 0.0 | 0.0 | 0.0 | 0.0 | 0.0 | 0.0 | — | 0.0 | 0.0 | 0.0 | 0.0 |
| Air | 0.0 | 0.0 | 0.0 | 0.0 | 0.0 | 0.0 | 0.0 | — | 0.0 | 0.0 | 0.0 | 0.0 |
| Total | 12.5 | 100.0 | 6.6 | 100.0 | 5.8 | 100.0 | 0.0 | — | 134.8 | 100.0 | 134.8 | 100.0 |
| Pressure | 3.0 | kg/cm2G | −0.7 | kg/cm2G | 10.0 | kg/cm2G | | kg/cm2G | 10.0 | kg/cm2G | 10.0 | kg/cm2G |
| | 0.294 | MPaG | −0.068 | MPaG | 0.981 | MPaG | | MPaG | 0.981 | MPaG | 0.981 | MPaG |
| Temperature | 115 | °C. | 132 | °C. | 132 | °C. | | °C. | 132 | °C. | 132 | °C. |
| Density | — | | — | | 1226 | kg/m3 | — | | — | | — | |

EXPLANATION OF LETTERS OR NUMERALS

A Granulation step
B Recovery step
C Concentration step
1 Feed aqueous urea solution
2 Granular solid urea
3 Air
4 Granulation outlet gas (air containing urea dust and ammonia)
5 Makeup water (containing an acid)
6 Exhaust gas
7 Aqueous recovered-urea solution (to be supplied to concentration step)
8 Water generated in concentration step
9 Concentrated aqueous recovered-urea solution (containing an ammonium salt)
10 Low ammonium salt concentration aqueous urea solution
11 Feed aqueous urea solution mixed with concentrated aqueous recovered-urea solution
12 The rest of the solution of line 11 after a part of this solution is branched to line 10
13 Aqueous recovered-urea solution (obtained from recovery step)
15 Part of feed aqueous urea solution (to be transferred to granulation step)
16 Rest of feed aqueous urea solution (low ammonium salt concentration aqueous urea solution)

What is claimed is:

1. A method for continuously granulating urea, comprising
    a granulation step of producing granular solid urea from a feed aqueous urea solution by using air, and discharging air containing urea dust and ammonia,
    a recovery step of recovering urea dust and ammonia from air containing urea dust and ammonia discharged from the granulation step, by use of an aqueous solution containing an acid, so as to obtain an aqueous recovered-urea solution which is an aqueous solution containing urea and an ammonium salt;
    an ammonium salt concentration adjustment step of mixing the aqueous recovered-urea solution which is obtained from the recovery step with an aqueous urea solution having a lower ammonium salt concentration as compared to that of the aqueous recovered-urea solution, so as to adjust the ammonium salt concentration of the aqueous recovered-urea solution;
    a concentration step of concentrating the aqueous recovered-urea solution which is obtained from the ammonium salt concentration adjustment step by vaporizing water which is contained in the aqueous recovered-urea solution which is obtained from the ammonium salt concentration adjustment step, so as to obtain a concentrated aqueous recovered-urea solution; and
    a mix step of mixing the concentrated aqueous recovered-urea solution with the feed aqueous urea solution before the feed aqueous urea solution is fed to the granulation step,
    wherein the ammonium salt concentration of the concentrated aqueous recovered-urea solution is 7 mass % or less.

2. The method according to claim 1, wherein, in the ammonium salt concentration adjustment step, a part of the feed aqueous urea solution, before or after the concentrated aqueous recovered-urea solution is mixed with it, is used as said aqueous urea solution having a lower ammonium salt concentration.

3. The method according to claim 1, further comprising, before the concentration step, a neutralization step of adding an alkali to the aqueous recovered-urea solution which is obtained from the recovery step to neutralize a residue of the acid in the aqueous recovered-urea solution, the neutralization step is conducted after the recovery step.

4. The method according to claim 1, further comprising a control step of controlling the ammonium salt concentration of the concentrated aqueous recovered-urea solution by manipulating the flow rate of said aqueous urea solution having a lower ammonium salt concentration which is to be mixed with the aqueous recovered-urea solution in the ammonium salt concentration adjustment step, based on the present value of the ammonium salt concentration of the concentrated aqueous recovered-urea solution.

5. The method according to claim 4, wherein, in the control step, the present value of the ammonium salt concentration of the concentrated aqueous recovered-urea solution is obtained based on the temperature and pressure of the water vaporization in the concentration step and the temperature and density of the concentrated aqueous recovered-urea solution.

6. The method according to claim 1, wherein the acid is at least one acid selected from the group consisting of sulfuric acid, nitric acid and phosphoric acid.

7. The method according to claim 1, further comprising a step of supplying the water, which is vaporized in the concentration step, to the recovery step.

8. The method according to claim 1, wherein the acid comprises sulfuric acid.

* * * * *